United States Patent [19]

Thomas

[11] 4,369,274

[45] Jan. 18, 1983

[54] HINDERED AMINE LIGHT STABILIZERS FOR POLYMERS

[75] Inventor: Walter M. Thomas, Darien, Conn.

[73] Assignee: American Cyanamid Company, Stamford, Conn.

[21] Appl. No.: 284,883

[22] Filed: Jul. 20, 1981

[51] Int. Cl.³ .................. C08K 5/34; C08F 126/06; C07D 211/94; C07D 211/66; C07D 211/62; C08F 39/04

[52] U.S. Cl. ........................ 524/99; 546/16; 546/221; 546/225; 546/242; 546/245; 526/265

[58] Field of Search ............... 260/45.8 NP; 546/16, 546/221, 225, 242, 245; 526/265; 524/99

[56] References Cited

U.S. PATENT DOCUMENTS

| | | | |
|---|---|---|---|
| Re. 30,385 | 8/1980 | Hillard et al. | 260/45.8 NP |
| 2,712,004 | 6/1955 | Thomas | 526/261 |
| 3,334,103 | 8/1967 | Feldman et al. | 260/45.8 NP |
| 3,534,048 | 10/1970 | Murayama et al. | 260/45.8 NP |
| 3,850,877 | 11/1974 | Cook | 260/45.8 N |
| 3,929,804 | 12/1975 | Cook | 260/45.8 NP |
| 4,210,612 | 7/1980 | Karrer | 526/265 |
| 4,239,891 | 12/1980 | Wiezer et al. | 260/45.8 NP |
| 4,276,401 | 6/1981 | Karrer | 526/265 |

*Primary Examiner*—V. P. Hoke
*Attorney, Agent, or Firm*—Steven J. Hultquist

[57] ABSTRACT

Compounds of the formula

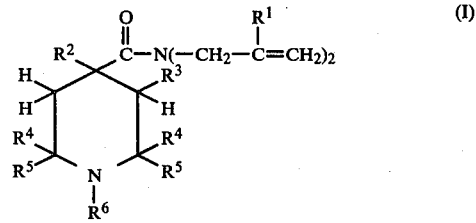

and polymers thereof are useful as ultraviolet radiation stabilizers for polymers.

11 Claims, No Drawings

HINDERED AMINE LIGHT STABILIZERS FOR POLYMERS

This invention relates to certain novel polymerizable compounds, to polymers thereof, and to their use as light stabilizers for polymers. More particularly, this invention relates to novel monomeric compounds of the formula (I)

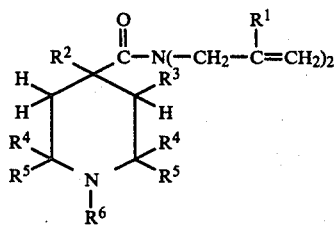

wherein $R^1$ represents hydrogen, or $C_1$-$C_4$ alkyl; $R^2$ represents hydrogen, hydroxy, or $C_1$-$C_8$ alkoxy; $R^3$ represents hydrogen, $C_1$-$C_8$ alkyl, or benzyl; $R^4$ and $R^5$ independently represent $C_1$-$C_8$ alkyl, benzyl, or phenethyl, or together with the carbon to which they are attached form a $C_5$-$C_{10}$ cycloalkyl; and, $R^6$ represents hydrogen, $C_2$-$C_3$ hydroxyalkyl, $C_1$-$C_8$ alkyl, hydroxy, or oxyl; and to polymers derived from said monomers. The invention also relates to the use of such monomers and polymers for stabilizing polymers, particularly polyolefins, against degradation by ultraviolet radiation.

Stabilizers for synthetic and naturally occurring polymers, including UV stabilizers, have been the subject of continuing investigation for many years, and numerous compounds have been suggested for such purpose. Recent patent literature has described a considerable number of stabilizer compounds which contain a hindered amine moiety, such as

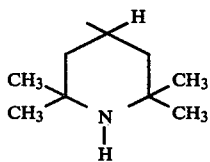

U.S. Pat. No. 3,705,166 discloses polymer compositions stabilized against photo-deterioration by incorporating therein a 4-acrylamidopiperidine, such as 4-acrylamido-2,2,6,6-tetramethylpiperidine, shown below.

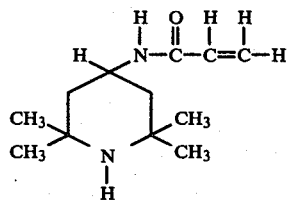

U.S. Pat. No. 2,712,004 discloses the polymerization of melamines containing N-allyl substituents.

U.S. Pat. No. Re. 30,385 discloses the use of esters of 2,2,6,6-tetraalkyl-4-carboxypiperidines as light stabilizers for synthetic polymers. Among those mentioned is allyl 2,2,6,6-tetramethylpiperidine-4-carboxylate. However, this compound does not polymerize. Since none has been found to be completely satisfactory, research continues in order to find compounds or combinations of compounds which will be more satisfactory. The present invention arose out of such research and resulted in the discovery of novel compounds which stabilize polymers against degradation by ultraviolet light.

The stabilizers of the present invention offer the following advantages:

(1) excellent light-stabilizing activity,
(2) excellent compatibility with resins,
(3) low volatility,
(4) low extractability from polymers by laundering or dry cleaning, and
(5) excellent oven-aging stability.

The compounds of formula (I) may be prepared by reacting a compound of formula (II)

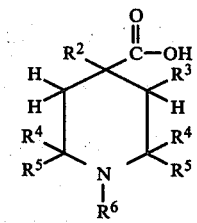

wherein $R^2$, $R^3$, $R^4$, $R^5$, and $R^6$ are as previously defined, with thionyl chloride or methyl alcohol to prepare the corresponding acid chloride or methyl ester, and reacting either of the latter with an amine of formula (III),

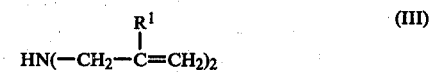

wherein $R^1$ is as previously defined, by conventional methods, and recovering the desired product.

The intermediate carboxylic acid (II) wherein $R^2$ is hydrogen may be prepared in accordance with procedures similar to those described by Simchen et al. in Synthesis, 1975, No. 9, pages 605–607, whereby the appropriate 4-bromo-piperidine is reacted with a tetraalkylammonium cyanide, such as tetraethylammonium cyanide, in a suitable solvent, such as dichloromethane, acetonitrile or dimethyl sulfoxide, followed by hydrolysis of the nitrile to the desired carboxylic acid (II).

Compounds of formula (II) wherein $R^2$ is hydroxy may also be prepared in accordance with procedures similar to those described by Nazarov et al, J. Gen. Chem. U.S.S.R. (English), 26, 3877–3889 (1956), whereby 2,2,6,6-tetramethyl-piperidin-4-one is reacted with potassium cyanide in the presence of an acid to produce the corresponding cyanohydrin which may then be hydrolyzed to the hydroxy acid.

Illustrative examples of suitable compounds of formula (I) include the following:

4-[(diallylamino)carbonyl]-2,2,6,6-tetramethylpiperidine,

4-[(diallylamino)carbonyl]-1,2,2,6,6-pentamethylpiperidine,

4-[(diallylamino)carbonyl]-1-oxyl-2,2,6,6-tetramethylpiperidine,

4-[(diallylamino)carbonyl]-1-hydroxy-2,2,6,6-tetramethylpiperidine,

4-[(diallylamino)carbonyl]-1-(2-hydroxyethyl)-2,2,6,6-tetramethylpiperidine,
4-[(dimethallylamino)carbonyl]-2,2,6,6-tetramethylpiperidine,
4-[(diallylamino)carbonyl]-2,6-di-n-butyl-2,6-dimethylpiperidine,
4-[(diallylamino)carbonyl]-2,2,6,6-tetraethylpiperidine,
4-[(diallylamino)carbonyl]-2,2,3,6,6-pentamethylpiperidine,
4-[(diallylamino)carbonyl]-2-benzyl-2,6,6-trimethylpiperidine,
15-[(diallylamino)carbonyl]-7-azadispiro[5.1.5.3]hexadecane,
4-[(diallylamino)carbonyl]-2-phenethyl-2,6,6-trimethylpiperidine,
4-[[bis(2-ethyl-2-propenyl)amino]carbonyl]-2,2,6,6-tetramethylpiperidine,
4-[[bis(2-n-butyl-2-propenyl)amino]carbonyl]-2,2,6,6-tetramethylpiperidine,
4-[(diallylamino)carbonyl]-4-hydroxy-2,2,6,6-tetramethylpiperidine,
4-[(diallylamino)carbonyl]-4-methoxy-2,2,6,6-tetramethylpiperidine,
4-[(diallylamino)carbonyl]-4-octyloxy-2,2,6,6-tetramethylpiperidine,
and the like.

In preparing the polymers of the present invention, a monomer of formula (I), or a mixture of a monomer of formula (I) and any copolymerizable comonomer, is polymerized employing an effective amount of a polymerization catalyst. Suitable polymerization catalysts include 2,2'-azobisisobutyronitrile, di-(t-butyl)peroxide, dilauryl peroxide, lauroyl peroxide, benzoyl peroxide, acetylperoxide, t-butyl hydrogen peroxide, ammonium persulfate, potassium persulfate, and the like. The preferred catalyst is 2,2'-azobisisobutyronitrile.

The monomer of formula (I) may be homopolymerized or copolymerized by utilizing a copolymerizable comonomer, in emulsion or solution by conventional methods. Suitable comonomers are disclosed in U.S. Pat. No. 2,712,004, the general disclosure of which is hereby incorporated herein by reference.

The compounds and polymers of this invention are useful as light stabilizers for thermoplastic substrates such as polyolefins, polyesters, polyethers, polyurethanes, polystyrenes, high-impact polystyrenes, and the like. Preferably, the thermoplastic substrate is a polyolefin.

Other organic materials susceptible to degradation by the effects of light, the properties of which are improved by the incorporation therein of a polymer of this invention, include natural and synthetic rubbers; the latter include, for example, homo-, co- and terpolymers of acrylonitrile, butadiene and styrene, and blends thereof.

The compounds of formula (I), and polymers therefrom, are particularly useful in polyolefins, such as polyethylene, polypropylene, polybutylene, and the like, and copolymers thereof.

Generally, the compositions comprise a polymer containing from about 0.1% to about 5% by weight of the compound of formula (I), or polymer therefrom, based on the weight of the polymer.

Preferably, the composition comprises a polyolefin containing from about 0.2% to about 2% by weight of the compound of formula (I), or polymer therefrom, based on the weight of the polyolefin.

Optionally, the compositions may contain other additives, especially additives useful in polyolefins, such as antioxidants, supplemental light stabilizers, plasticizers, flame retardants, antistatic and antislipping agents, fillers, dyes, pigments, and the like.

Suitable antioxidants include those of the hindered phenol type, such as 2,6-di-t-butyl-p-cresol; 4,4'-methylenebis(2,6-di-t-butylphenol); 4,4'-methylenebis(2,6-diisopropylphenol); 2,4,6-tri-t-butylphenol; 2,2'-thiobis-(4-methyl-6-t-butylphenol); 1,3,5-tris(4-t-butyl-3-hydroxy-2,6-dimethylbenzyl)-1,3,5-triazine-2,4,6-(1H,3H,5H)-trione; octadecyl 2(3',5'-di-t-butyl-4'hydroxyphenyl)propionate, etc; esters of thiodipropionic acid, such as dilauryl thiodipropionate and distearyl thiodipropionate, etc; hydrocarbyl phosphites, such as triphenyl phosphite, trinonyl phosphite, diisodecyl pentaerythrityl diphosphite, diphenyldecyl phosphite, etc; and combinations thereof.

Suitable supplemental light stabilizers include those of the benzotriazole class, such as 2-(2'-hydroxy-5-t-octylphenyl)benzotriazole; 2-(2'-hydroxy-3',5'-di-t-butylphenyl)-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-dimethoxybenzophenone; hindered phenol esters, such as n-hexadecyl 3,5-di-t-butyl-4-hydroxybenzoate, and 2',4'-di-t-butylphenyl 3,5-di-t-butyl-4-hydroxybenzoate; metal complexes, such as nickel complexes of 2,2'-thiobis(4-t-octylphenol); nickel butylamine complex of 2,2'thiobis(4-t-octylphenol); nickel complexes of bis(4-t-octylphenyl)sulfone; nickel dibutyl dithiocarbamate; nickel salts of 4-hydroxy-3,5-di-t-butylbenzyl phosphonic acid monoalkyl esters where alkyl is methyl, ethyl, propyl, butyl, etc; nickel complex of 2-hydroxy-4-methylphenyl undecyl ketone oxime, etc. Further illustrative examples of suitable antioxidants and supplemental light stabilizers can be found in U.S. Pat. No. 3,723,427, columns 3 and 4 of U.S. Pat. Nos. 3,488,290 and 3,496,134, and in the other patents mentioned therein.

As with the compound of formula (I), or polymer therefrom, the additive is advantageously employed within the range from about 0.2% to about 2% by weight, based on the weight of the untreated polymer.

The compound of formula (I), or polymer therefrom, may be incorporated into the polymeric substrate by any of the known techniques for compounding additives with a polymer. For example, the compound of formula (I), or polymer therefrom, and the additive may be compounded by dry blending with the substrate in powder or granular form, followed by milling, Banbury mixing, molding, casting, extruding, swelling, and the like. Alternatively, the compound of formula (I), or polymer therefrom, may be added, as a solution or slurry in a suitable inert solvent, or dispersant, to the polymeric substrate in powder or granular form, the whole mixed intimately in a mixer, and the solvent subsequently removed. As a further possibility, the compound of formula (I), or polymer therefrom, may be added to the polymeric substrate during the preparation of the latter, for instance at the latex stage of polymer production, to provide prestabilized polymer material.

The following examples illustrate the present invention. All parts and percentages are by weight unless otherwise indicated.

EXAMPLE 1

Preparation of 4-[(Diallylamino)carbonyl]-2,2,6,6-tetramethylpiperidine

4-Carboxy-2,2,6,6-tetramethylpiperidine (100 grams; 0.5405 mole) is added to thionyl chloride (300 mls) in portions and the reaction mixture is heated at reflux for 3 hours. The thionyl chloride is then removed by distillation, the last traces being removed by azeotropic distillation with toluene. The residual acid chloride is slurried in dichloromethane (300 mls), and a solution of diallylamine (105 grams; 1.081 mole) in dichloromethane (100 mls) is slowly added thereto while stirring and allowing the temperature to rise. Upon completion of the addition, the reaction mixture is heated at reflux for 18 hours, cooled to room temperature, and treated successively with 100 mls of water, and 5 N sodium hydroxide, while stirring, to adjust the pH to about 11. The organic phase is separated, and washed with dilute aqueous sodium hydroxide having a pH of 11. The aqueous phase is separated and the organic phase is washed twice with 100-ml portions of very dilute aqueous hydrogen peroxide (5 mls of 30% hydrogen peroxide diluted to 100 mls with water). After the second washing, the organic phase is washed twice with water, treated with activated carbon, dried over anhydrous magnesium sulfate, filtered and evaporated under vacuum to remove dichloromethane and unreacted diallylamine. The residue is then distilled under vacuum to obtain 60 grams of the desired product, bp 118°–128° C. at 0.05 mm of mercury, mp 64°–67° C.

EXAMPLE 2

Polymerization of 4-[(Diallylamino)carbonyl]-2,2,6,6-tetramethylpiperidine

The product of Example 1 (52.5 grams) is added to toluene (60 grams) and azobisisobutyronitrile (1.58 grams) is added to the resulting mixture. The mixture is purged with nitrogen for 45 minutes, then heated at 65° C. for 24 hours and at 75° C. for 24 hours while slowly passing nitrogen over the surface of the reaction mixture. Additional azobisisobutyronitrile (0.53 gram) is added to the reaction mixture and heating is continued at 75° C. for an additional 22 hours. Addition of the reaction mixture to cold petroleum ether results in the formation of a precipitate which is recovered by filtration and dried in a vacuum oven to obtain 15.8 grams of a product having a number average molecular weight of 1084.

EXAMPLE 3

Preparation of 4-[(Diallylamino)carbonyl]-1,2,2,6,6-pentamethylpiperidine

4-[(Diallylamino)carbonyl]-2,2,6,6-tetramethylpiperidine (58.0 grams; 0.219 mole) is slurried in 37% formaldehyde (98.6 mls) at room temperature and 95% formic acid (17.4 mls) is added thereto. The mixture is heated at reflux for 18 hours and the resulting two-phase reaction mixture is adjusted to pH 11–12 by adding 50% sodium hydroxide. The mixture is extracted with dichloromethane and the organic extracts are combined and evaporated to obtain a clear liquid which on distillation affords 58.3 grams of the desired product which boils at 118°–125° C. at 0.10–0.15 mm of mercury.

EXAMPLE 4

Polymerization of 4-[(Diallylamino)carbonyl]-1,2,2,6,6-pentamethylpiperidine The product of Example 3 (51.6 grams) is treated with azobisisobutyronitrile (1.548 grams), and the mixture is purged with nitrogen for two hours. The mixture is then heated to 65° C. and maintained at 65° C. under a nitrogen atmosphere for 48 hours. At this point, additional azobisisobutyronitrile (0.516 gram) is added to the mixture and heating at 65° C. is continued for an additional 67 hours under nitrogen. The reaction mixture is then added to cold hexane, and the resulting precipitate is recovered by filtration and dried in a vacuum oven to obtain 18 grams of a product having a number average molecular weight of 1178.

EXAMPLES 5–8

Testing in Polypropylene

The compounds of Examples 1–4 (0.25 gram) are separately dry blended with a mastermix of 100 grams of unstabilized polypropylene (Pro-fax ® 6401) and 0.1 gram of a processing antioxidant, 2,4,6-tri-t-butylphenol. The blend is milled at 350°–370° F. for five minutes, and then compression molded at 400° F. into a film 4–5 mils thick. The film and a control film, identically prepared without the compound under test, are exposed to a xenon arc in an Atlas Weather-Ometer ® until they fail. A film is considered as having failed when the carbonyl content of the infrared absorption spectrum increases by 0.10-weight percent, a generally accepted point of film embrittlement.

The data in Table I show the number of hours required to increase the carbonyl content by 0.1% by weight for the compounds under test and a control film.

TABLE I

| Example | Additive | Hours to Failure |
|---|---|---|
| 5 | Product of Example 1 | not available |
| 6 | Product of Example 2 | 800 |
| 7 | Product of Example 3 | not available |
| 8 | Product of Example 4 | 800 |
|   | None | <200 |

What is claimed is:
1. A compound of the formula (I)

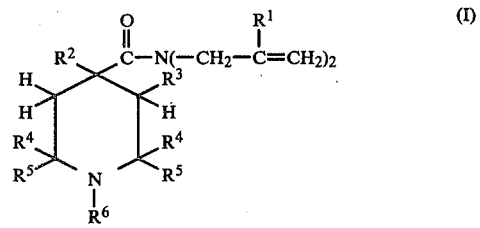

wherein $R^1$ represents hydrogen, or $C_1$–$C_4$ alkyl; $R^2$ represents hydrogen, hydroxy, or $C_1$–$C_8$ alkoxy; $R^3$ represents hydrogen, $C_1$–$C_8$ alkyl, or benzyl; $R^4$ and $R^5$ independently represent $C_1$–$C_8$ alkyl, benzyl, or phenethyl, or together with the carbon to which they are attached form a $C_5$–$C_{10}$ cycloalkyl; and, $R^6$ represents hydrogen, $C_2$–$C_3$ hydroxyalkyl, $C_1$–$C_8$ alkyl, hydroxy, or oxyl.

2. The compound of claim 1 wherein $R^3$ is hydrogen and $R^4$ and $R^5$ are each methyl.

3. The compound of claim 1 wherein $R^1$, $R^2$, and $R^3$ are hydrogen; $R^4$ and $R^5$ are each methyl; and $R^6$ is hydrogen or methyl.

4. A homopolymer of the compound of claim 1, 2 or 3.

5. A copolymer comprising the compound of claim 1, 2 or 3 and copolymerized therewith, an ethylenically unsaturated monomer.

6. A method of stabilizing a polymer which is normally subject to degradation by ultraviolet radiation which comprises incorporating into said polymer an ultraviolet stabilizingly effective amount of a compound or polymer of a compound of claim 1.

7. The method of claim 6 wherein the stabilizer is incorporated in a concentration of from about 0.2% to 2% based on the weight of the polymer.

8. The method of claim 6 wherein the polymer being stabilized is a polyolefin.

9. The method of claim 8 wherein the polyolefin is polypropylene.

10. The method of claim 6 wherein the stabilizer compound or polymer thereof, $R^3$ is hydrogen and $R^4$ and $R^5$ are each methyl.

11. The composition produced by the method of claim 6.

* * * * *